(12) United States Patent
Windolf et al.

(10) Patent No.: US 12,324,613 B2
(45) Date of Patent: Jun. 10, 2025

(54) BIPHASIC BONE PLATE

(71) Applicant: AO Technology AG, Chur (CH)

(72) Inventors: Markus Windolf, Davos (CH); Devakara Epari, Newstead (AU)

(73) Assignee: AO Technology AG, Chur (CH)

( * ) Notice: Subject to any disclaimer, the term of this patent is extended or adjusted under 35 U.S.C. 154(b) by 244 days.

(21) Appl. No.: 17/780,576

(22) PCT Filed: Nov. 24, 2020

(86) PCT No.: PCT/CH2020/050012
§ 371 (c)(1),
(2) Date: May 27, 2022

(87) PCT Pub. No.: WO2021/102591
PCT Pub. Date: Jun. 3, 2021

(65) Prior Publication Data
US 2023/0000534 A1    Jan. 5, 2023

(30) Foreign Application Priority Data
Nov. 29, 2019 (CH) ...................................... 01515/19

(51) Int. Cl.
*A61B 17/80* (2006.01)
*A61B 17/00* (2006.01)

(52) U.S. Cl.
CPC .............................. *A61B 17/8085* (2013.01); *A61B 2017/00526* (2013.01)

(58) Field of Classification Search
CPC . A61B 17/80; A61B 17/8023; A61B 17/8061; A61B 17/8085; A61B 17/842
See application file for complete search history.

(56) References Cited

U.S. PATENT DOCUMENTS

| | | | |
|---|---|---|---|
| 8,979,901 B2 * | 3/2015 | Trieu | A61B 17/7046 606/264 |
| 2007/0173839 A1 | 7/2007 | Running et al. | |
| 2015/0039033 A1 | 2/2015 | Biedermann | |
| 2018/0263669 A1 * | 9/2018 | Peterson | A61B 17/8605 |

FOREIGN PATENT DOCUMENTS

| | | | |
|---|---|---|---|
| EP | 1221308 A1 | 7/2002 | |
| WO | WO-2017024416 A1 * | 2/2017 | A61B 17/80 |

OTHER PUBLICATIONS

International Search Report dated Mar. 5, 2021 filed in PCT/CH2020/050012.

* cited by examiner

*Primary Examiner* — Larry E Waggle, Jr.
(74) *Attorney, Agent, or Firm* — Rankin, Hill & Clark LLP (57) ABSTRACT

Bone plate (1) with a lower surface (2), an upper surface (3), a maximum thickness measured between the lower and upper surfaces a left lateral surface (4), a right lateral surface (5), a longitudinal axis (6) and a plurality of plate holes (7) miming from the lower surface to the upper surface, the bone plate further having a slot (8) in the lower surface extending from the left lateral surface to the right lateral surface having a width measured in a plane parallel to the longitudinal axis and a central plane (16) between the lateral surfaces, wherein (i) the hollow space defined by the slot extends in the form of a straight cylinder from the left lateral surface to the right lateral surface and (ii) the slot comprises an undercut feature (9) limiting the opening of the slot when the bone plate is bent longitudinally in a direction aimed at widening the slot.

20 Claims, 3 Drawing Sheets

BIPHASIC BONE PLATE

BACKGROUND OF THE INVENTION

1. Field of the Invention

The invention relates to a bone plate according to the preamble of claim 1 and to a method of manufacturing the bone plate according to the preamble of claim 10.

Bone plates which exhibit a biphasic stiffness behavior promote secondary bone healing. These bone plates permit required interfragmentary motion at low functional loading (flexible phase), and limit said motion to a maximum when the slot closes at higher magnitudes of functional loading (rigid phase). These bone plates, hence, provide controlled motion to the bone fracture largely independent from the magnitude of functional loading. Thereby (i) healing complications caused by mechanically adverse conditions can be avoided and (ii) the average time to bony union may be shortened. It was found that interfragmentary motion of 0.5 mm (0.2-1 mm) provides a good healing outcome in different fracture sizes (1, 2 and 6 mm cover the vast majority of fractures). Known bone plates with an optimized slot width avoid overstimulation of the fracture, which could lead to healing complications such as hypertrophic delayed- and non-unions.

2. Description of the Related Art

A biphasic bone plate is known form WO 2017/024416. In order to provide resistance against tensile forces and valgus bending of the bone plate this known bone plate comprises a slot having a lower section which extends from the lower surface of the bone plate towards the upper surface and which extends across the bone plate along the form of an "Ω" in a view onto the lower surface of the bone plate. This Ω-shape is formed by a nose which protrudes from one of the rigid sections of the bone plate along the longitudinal axis of the bone plate and which has an enlarged free end and by an concavely formed adjoining end of the other rigid section, wherein the concavity forms an encompassment for the nose so that movement of the nose relative to the encompassment is limited in both directions along the longitudinal axis of the bone plate. Further, a central section of the slot has a width increasing towards the upper section of the slot and the upper section of the slot has two curved legs extending in the direction of the longitudinal axis of the bone plate. The lower section of the slot has an essentially cylindrical shape which has an Ω-shaped base on the lower surface of the bone plate and which has a peripheral surface extending vertically, i.e. orthogonally to the lower surface of the bone plate. Contrarily, the central section and the upper section of the slot each have an essentially cylindrical shape having their bases on the lateral sides of the bone plate while their peripheral surfaces extend laterally, i.e. parallel to a transverse axis of the bone plate which extends orthogonally to the longitudinal axis between the two lateral surfaces of the bone plate. Due to the fact that the central axes of the cylinders of the central and upper sections of the slot extend orthogonally to the central axis of the cylinder of the lower section of the slot, the lower section and the central and upper sections have to be manufactured in separate and subsequent working processes resulting in a complex and costly manufacture of the slot.

The window size of the plate according to WO 2017/024416 is solely determined by the width W of the slot feature at the lower surface of the plate. It is hence intuitive to limit not only the closing but also the opening of the slot by an undercut feature located at the lower plate surface (as disclosed in the previous invention).

BRIEF SUMMARY OF THE INVENTION

It is an object of the invention to provide a bi-phasic bone plate and a method for its manufacture which permits a production of the bone plate in a single manufacturing step without reducing the resistance of the bi-phasic bone plate against tensile forces and valgus bending. A further object of the invention is the possibility of manufacturing small slot width (of less than 0.3 mm) without the necessity of assembling different plate parts.

The invention solves the posed problem with a bone plate comprising the features of claim 1 and with a method of manufacturing the bone plate comprising the features of claim 10.

The advantages of the bone plate according to the invention can be essentially seen therein that:
  a straight slot can be produced in a single manufacturing step from a single work piece using a standard wire-erosion or waterjet cutting process. Production time, complexity and, hence, production costs are thereby reduced; and
  catastrophic failure of the bone plate under unphysiological loading conditions (valgus bending) can be prevented.

Furthermore the inventive idea to shift the undercut feature (opening limiter) away from the lower plate surface to a different location and orientation produces the additional unexpected advantages of:
  Producibility of the slot incl. undercut feature in a single manufacturing step with a well-established and robust manufacturing process, such as wire-erosion.
  Producibility of the slot incl. undercut feature with a desired slot width of <0.3 mm. Other manufacturing processes, e.g. sink erosion are not capable of generation such narrow slots. The alternative, assembly from different parts, can be avoided.
  The contact area at the lower plate surface at slot closing becomes a flat surface over the entire width of the bone plate, which allows for uniform and distributed contact, limiting particle wear generation. A non-straight but curved slot (e.g. omega) does not allow uniform slot closing due to the non-constant bent-line of the bone plate.

The bone plate according to the invention exhibits a significant increase in strength [>2× ultimate load to failure (off-centric axial compression)] and fatigue performance (>4× cycles to failure) as compared to a standard bone plate. This reduces the risk for clinical implant failure significantly.

Further advantageous embodiments of the invention can be commented as follows:

In a special embodiment the width W of the slot measured in a plane parallel to the longitudinal axis and to the central plane between the lateral surfaces is variable. This configuration permits the advantage that the slot width may significantly widen towards the upper surface e.g. in a T-shape to form a stress distribution feature.

In another embodiment the undercut feature has an S-shape, a Z-shape or an Ω-shape in a plane parallel to the longitudinal axis and to the central plane between the lateral surfaces. Due to the S-shape, Z-shape or Ω-shape of the undercut feature two adjoining projections are formed which additionally provide resistance against torsion of the bone plate.

In a further embodiment the dimensions of the undercut feature are chosen such that lengthening of the lower surface is limited to at most 3 mm, preferably at most 1 mm when the bone plate is bent longitudinally in a direction aimed at widening the slot.

In a further embodiment the slot has a width W in the range of 0.1 to 1.3 mm, preferably in the range of 0.15-0.30 mm measured at the lower surface of the bone plate in the direction of the longitudinal axis.

In a further embodiment the slot is configured with the shape of a "T" or of an "L" in an upper portion of the bone plate, wherein the free end of the vertical leg of the "T" or "L" runs into the undercut feature of the slot and the two horizontal legs of the "T" or the horizontal leg of the "L" extend in the direction of the longitudinal axis of the bone plate and are preferably curved.

In yet a further embodiment the walls of the slot at the lower surface of the bone plate are angulated with respect to each other such that they become parallel upon closing of the slot. The slot deforms through bending of the bone plate which leads to tilting of the originally parallel walls and hence leads to a line contact of the slot at closure. This again may generate accentuated metal wear at the contact area. Creating an angulated slot for compensating the tilt increases the contact area and hence reduces wear.

In another embodiment the dimensions of the slot are chosen such that the length of the lower surface is shortened at most 1 mm, preferably at most 0.3 mm upon complete closure of the slot at the lower surface of the bone plate so that the width W measured at the lower surface is equal to 0.

In another embodiment the slot allows the plate to bend longitudinally at least to the amount of 1.0°, preferably at least 1.5°.

In a further embodiment the bone plate comprises more than one slot.

In another embodiment the bone plate additionally comprises means for attachment of a bone healing sensor, preferably in the in the form of threaded screw holes apt to receive fasteners.

In another embodiment the bone plate is configured in such a way that the bending stiffness in the flexible section is reduced by 75% compared to a conventional bone plate without a slot when the width W of the slot measured at the lower surface of the bone plate is greater than 0 and is increased by 75% compared to a conventional bone plate without a slot when the width W of the slot measured at the lower surface of the bone plate is equal to 0 under off-centric axial compression. The aforementioned increase of the bending stiffness of about 75% compared to a conventional bone plate without a slot highly depends on the loading mode and can be significantly higher.

In another embodiment the dimensions of the slot are chosen such that the bone plate is allowed to bend longitudinally—additionally to the intrinsic bendability of the unslotted plate—at most to the amount of 20°, preferably at most to the amount of 10°

In another embodiment the width W of the slot measured at the lower surface of the bone plate in the direction of the longitudinal axis is larger than 0.25 mm, preferably larger than 0.20 mm.

In again another embodiment the width W of the slot measured at the lower surface of the bone plate in the direction of the longitudinal axis is smaller than 0.30 mm, preferably smaller than 0.25 mm.

In a further embodiment the bone plate has a maximum thickness in the range of 6 mm-13 mm.

In a further embodiment the bone plate has a thickness in the range of 10 mm-12 mm, preferably for use on the femur.

In a further embodiment the bone plate has a thickness in the range of 4 mm-9 mm preferably for use on the humerus or tibia.

In another embodiment the bone plate has a width measured at the lower surface at the position of the slot and vertically to the longitudinal axis in the range of 14 mm-22 mm, preferably in the range of 17 mm to 21 mm.

In another embodiment a force in the range of 50-400 N, preferably in the range of 100-300 N, acting essentially parallel to the longitudinal axis of the bone plate with an offset of 10 mm to 30 mm from the lower surface of the bone plate is sufficient to close the slot at the lower surface of the bone plate so that the width W is equal to 0.

In a further embodiment the slot has a curved-shaped form seen in a longitudinal cross-section of the bone plate, the curved-shaped form enlarging from the lower surface towards the upper surface.

Preferably, the plate thickness T gradually decreases from the slot towards both ends of the bone plate.

In a further embodiment at least one of the plurality of plate holes is configured to receive an angular stable locking screw at a predefined angle.

In a further embodiment at least one of the plurality of plate holes is configured to receive a variable angle locking screw.

In another embodiment the plate holes have different sizes to receive bone screws of different diameters.

Preferably, the bone plate is made of titanium or a titanium alloy and preferably from stainless steel.

Preferably, the bone plate is used for the treatment of bone fractures.

In a further embodiment the slot is fully or partially covered by an elastic biocompatible membrane, the membrane preferably being impermeable for micro and nano metallic wear particles. By this means the advantage can be achieved that potential wear particles generated through intermittent slot closing contact can be confined in the membrane.

In a further embodiment the bone plate is pre-contoured to a statistically derived shape of a specific anatomical region.

According to a further aspect to the invention a method of manufacturing the bone plate according to the invention is provided, wherein the slot is formed using a wire-erosion or waterjet cutting process.

Preferably, the slot is generated by penetrating the bone plate with an eroding or cutting instrument into one of the lateral surfaces and guiding it in a directed straight manner to the opposite lateral surface thereby creating a through going slot.

A BRIEF DESCRIPTION OF THE DRAWINGS

A special embodiment of the invention will be described in the following by way of example and with reference to the accompanying drawings in which.

DETAILED DESCRIPTION OF THE INVENTION

FIGS. 1-6 illustrate an exemplary embodiment of the bone plate 1 according to the invention including a lower surface 2, an upper surface 3, a maximum thickness T measured between the lower and upper surfaces 2; 3, a left lateral surface 4, a right lateral surface 5, a longitudinal axis 6 and a plurality of plate holes 7 running from the lower surface 2 to the upper surface 3. Furthermore, the bone plate 1 comprises a slot 8 in the lower surface 2 extending from the left lateral surface 4 to the right lateral surface 5. The slot 8 has a width W of 0.15 mm measured in a plane parallel to the longitudinal axis 6 and a central plane 16 between the lateral surfaces 4,5. The hollow space defined by the slot 8 extends in the form of a straight cylinder (also called right cylinder) from the left lateral surface 4 to the right lateral surface 5, wherein the slot 8 comprises an undercut feature 9 limiting the opening of the slot 8 when the bone plate 1 is bent longitudinally in a direction aimed at widening the slot 8.

Exemplarily, but not limiting, the undercut feature 9 of the slot 8 has an S-shape in a plane parallel to the longitudinal axis 6 and to the lateral surfaces 4,5 so that by means of the two bows of the S-shape two complementary projections 13a,13b (FIG. 5) are formed. The undercut feature 9 of the slot 8 is located in a lower portion of the bone plate 1, i.e. in a portion of the bone plate 1 closer to the lower surface 2 of the bone plate 1.

The S-shape is configured as an "S" being upright in the direction of the longitudinal axis 6 in such a way that one bow of the "S" extends into a vertical section of the slot 8, which extends from the lower surface 2 of the bone plate 1 towards the upper surface 3 of the bone plate 1 and which has a width W measured at the lower surface 2 of the bone plate 1 in a plane parallel to the longitudinal axis 6 and the central plane 16 between the lateral surfaces 4,5. The complementary projections 13a,13b formed by the S-shaped slot 8 are spaced apart from each other—in case of an unloaded bone plate 1—by a width of the slot 8 which may be smaller or slightly larger than the width W of the slot 8 measured at the lower surface 2 of the bone plate 1, so that the two projections 13a,13b engage with each other from the left lateral surface 4 to the right lateral surface 5 when the bone plate 1 is bent in such a way that the tensile forces occur on the lower surface 2 of the bone plate 1 and therewith lock the bone plate 1 against further bending in this direction as well as against torsion around the longitudinal axis 6 of the bone plate 1.

In the embodiment illustrated in FIGS. 1-6 the slot 8 is configured with the shape of a "T" in an upper portion of the bone plate 1, i.e. in a portion of the bone plate 1 closer to the upper surface 3 of the bone plate 1. Thereby, the free end of the vertical leg of the "T" runs into the S-shaped portion of the slot and the two horizontal legs of the "T" are curved and extend in the direction of the longitudinal axis 6 of the bone plate 1.

Due to the slot 8 the flexural rigidity (also called bending stiffness) of the bone plate 1 is significantly reduced in the region of the slot 8 so that the bone plate 1 is divided into three longitudinal sections, namely a flexible section 10 in the region of the slot 8 and two rigid sections 11a, 11b whereof each one extends to one lateral end of the bone plate 1. The plate holes 7 are located in the rigid sections 11a, 11b so that bone fasteners extending through the plate holes 7 and fixed in bone fragments are arranged in the rigid sections 11a, 11b of the bone plate 1. Therefore, the load acting onto the bone plate 1 due to the weight of the patient or due to forces exerted by the patient is applied to the rigid sections 11a, 11b of the bone plate 1. In the flexible section 10 the bone plate 1 is formed as a beam shaped bridging portion 12 which is vertically limited by the top side, i.e. by the horizontal legs of the "T"-shape of the slot 6 and the upper surface 3 of the bone plate 1.

Due to the reduced flexural rigidity of the bridging portion 12 compared to the rigid sections 11a,11b of the bone plate 1 the bone plate 1 bends first in the flexible section 10. Under a bending load applied in this manner compressive and tensile forces develop in the direction of the longitudinal axis 6 which induce stresses on the bone plate 1. If the effect of the bending moment resulting from applied bending load tends to close the slot 8 the maximum compressive stress is found at the top side of the slot 6 while the maximum tensile stress is found at the upper surface 3.

The top side 14 of the slot 8 extends along the two horizontal legs of the "T". Because the deflection of the bridging portion 12 depends on a higher degree on the length of the bridging portion 12 than the stress induced on the bridging portion 12 via the bending moment the configuration of the flexible section 10 of the bone plate 1 can be optimized with respect to the desired deflection required for closing the slot 8 at the lower surface 2 of the bone plate 1 and with respect to the maximum stress occurring in the bridging portion 12. Furthermore, due the curved configuration of the two horizontal legs of the "T" the height of the bridging portion 12 measured between the top side 14 of the slot 8 and the upper surface 3 of the bone plate 1 varies along the length of the bridging portion 12 from a minimum height in the longitudinal middle plane of the bridging portion 12 to a maximum at the change-over from the bridging portion 12 to the rigid sections 11a, 11b of the bone plate 1. The flexural rigidity of the bridging portion 12 at a particular position along the longitudinal axis 6 is dependent on the height of the bridging portion 12 at this position so that the bridging portion 12 can be configured with a varying flexural rigidity where the variation of the flexural rigidity can be specifically adapted to optimize the stress distribution in the bridging portion 12.

Figure 7:
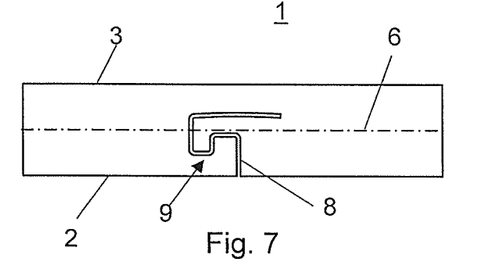
FIG. 7 illustrates a lateral view of a central portion of another embodiment of the bone plate according to the invention.

Alternatively, a similar effect—compared to the T-shape of the slot 8—can be achieved by a configuration of the slot 8 with the shape of an "L" in the upper portion of the bone plate 1, i.e. in a portion of the bone plate 1 closer to the upper surface 3 of the bone plate 1. Thereby, the free end of the vertical leg of the "L" runs into the S-shaped portion of the slot 8 and the horizontal leg of the "L" is straight and extends in the direction of the longitudinal axis 6 of the bone plate 1 (FIG. 7).

According to the Euler-Bernoulli bending theory the curvature of the neutral axis in the bridging portion 12 is proportional to the bending moment and inversely proportional to the flexural rigidity (bending stiffness), wherein the flexural rigidity is defined as the product E*I, where E is the elastic modulus or also called Young's modulus and I is the second moment of area of the cross-section of the bridging portion 12.

For the narrowing and the closure of the slot 8 the deflection of the bridging portion 12 is relevant only, while an eventual bending deformation of the rigid sections 11*a*, 11*b* of the bone plate 1 can be neglected.

The transition from the flexible phase to the rigid phase of the bone plate 1 occurs when the slot 8 closes at the lower surface 2 of the bone plate 1 and therefore depends on the deflection of the bridging portion 12 which is as described above a function of the bending moment, the flexural rigidity of the bridging portion 12 and the length thereof measured in the direction of the longitudinal axis 6 of the bone plate 1.

Figure 1:
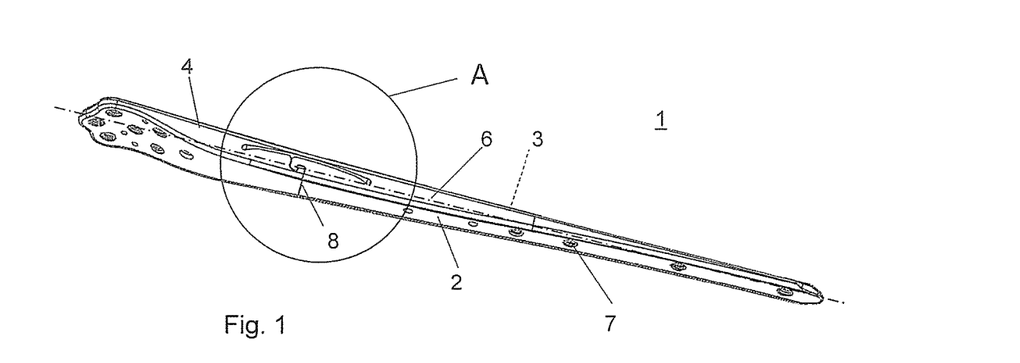
FIG. 1 illustrates a perspective view of an embodiment of the bone plate according to the invention.
Figure 2:
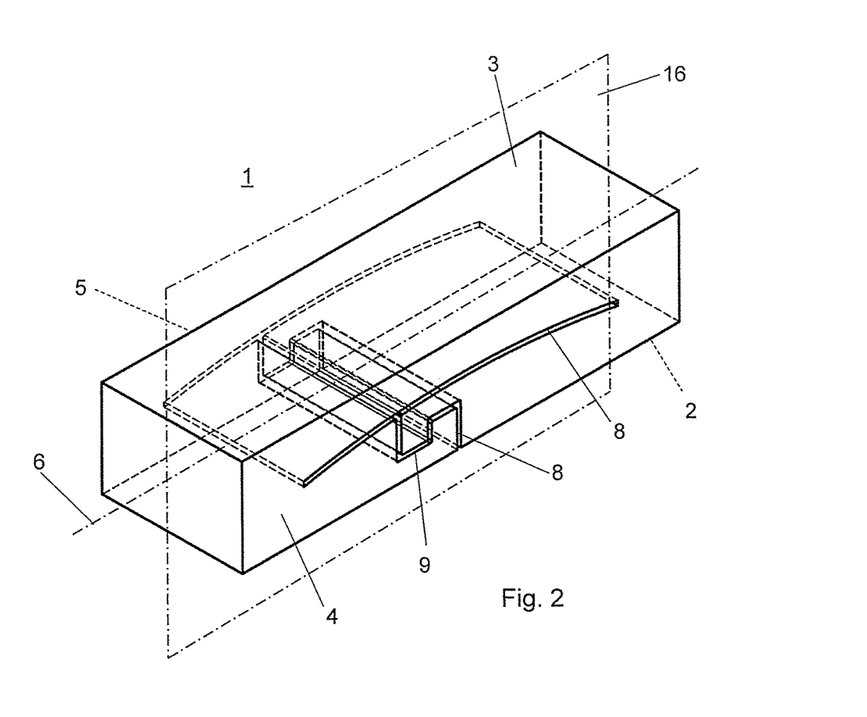
FIG. 2 illustrates a magnified view of detail A in FIG. 1.
Figure 3:
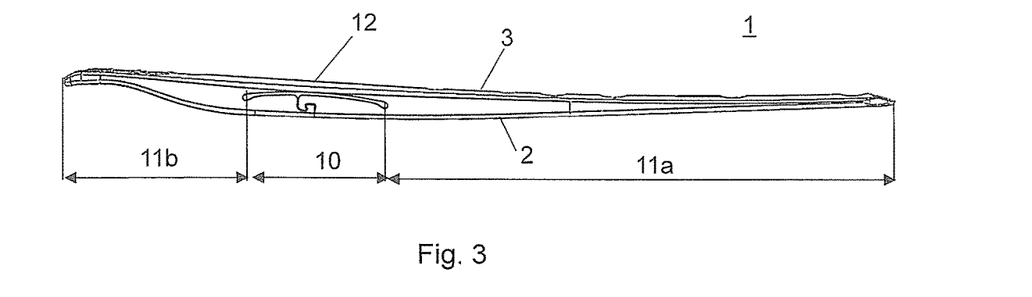
FIG. 3 illustrates a lateral view of the embodiment of FIG. 1.
Figure 4:
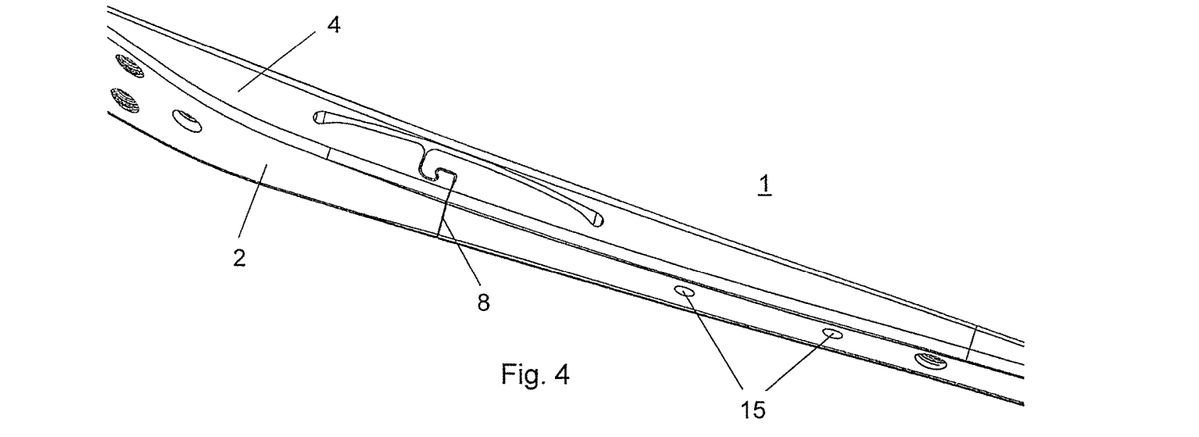
FIG. 4 illustrates a perspective view of a central portion of the embodiment of FIG. 1.
Figure 5:
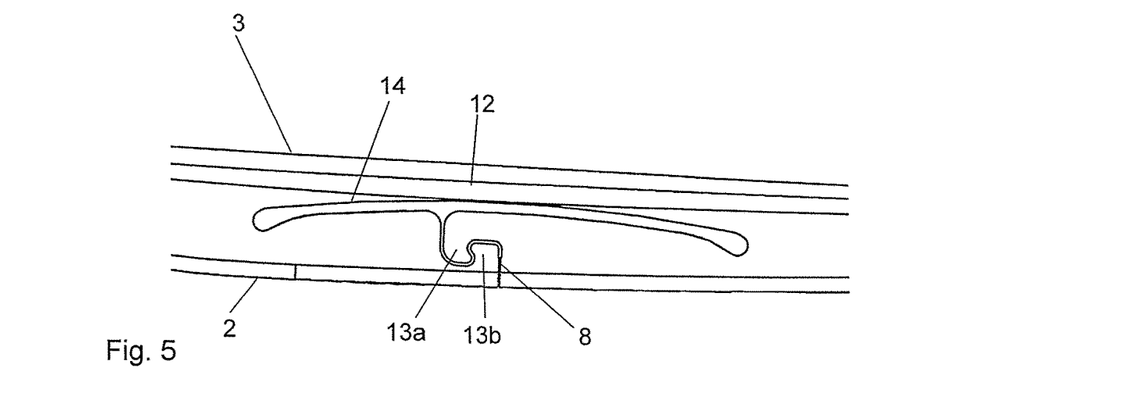
FIG. 5 illustrates a lateral view of a central portion of the embodiment of FIG. 1.
Figure 6:
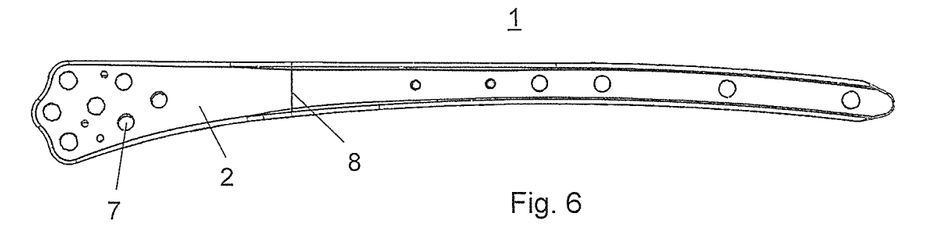
FIG. 6 illustrates a bottom view of the embodiment of FIG. 1.

Exemplarily, but not limiting, the embodiment of the bone plate 1 according to the invention as illustrated in FIGS. 1-6 is configured for an application on metaphyseal fractures, such as the distal femur, the proximal humerus or the distal/proximal tibia. One rigid section 11*b* of the bone plate 1 is spoon-shaped and the slot 8 is arranged closer to the spoon-shaped rigid section 11*b*. Further, the plate holes 7 in the spoon-shaped rigid section 11*b* are arranged in the enlarged portion which is terminally arranged on the bone plate 1 while the plate holes 7 in the other rigid section 11*a* are arranged along the longitudinal axis 4 of the bone plate 1 and evenly spaced from each other (FIG. 6). By these means the bone plate 1 is pre-contoured to a statistically derived shape of the specific anatomical region.

Exemplarily, but not limiting the bone plate 1 is made from stainless steel. In alternative embodiments the bone plate 1 may be made from titanium or a titanium alloy. The bone plate 1 has a plate thickness T which gradually decreases from the region with the slot 8 towards both ends of the plate 1. For the specific application of the bone plate 1 on the humerus or tibia the thickness T in the region of the slot 8 exemplarily, but not limiting, amounts to about 8 mm. Further, the bone plate 1 has exemplarily, but not limiting, a width measured at the lower surface 2 at the position of the slot 8 and vertically to the longitudinal axis 6 of about 17 mm. Alternatively, for use on the femur the bone plate 1 may have a plate thickness T in the region of the slot 8 of exemplarily, but not limiting, about 12 mm.

The bone plate 1 has a biphasic stiffness behavior to promote secondary bone healing, i.e. to permit required interfragmentary motion at low functional loading (flexible phase), and to limit this motion to a maximum when the slot closes at higher magnitudes of functional loading (rigid phase). The bending stiffness in the flexible section 10 is reduced by 75% compared to a conventional bone plate without a slot when the width W of the slot 8 measured at the lower surface 2 of the bone plate 1 is greater than 0 (flexible phase) and is increased by 75% compared to a conventional bone plate without a slot when the width W of the slot 8 measured at the lower surface 2 of the bone plate 1 is equal to 0 (rigid phase) in off-centric axial compression.

The plate holes 7 can be configured as variable angle holes. Alternatively, one or more of the plate holes 7 can be configured to receive an angular stable locking screw at a predefined angle. For this purpose the one or more plate holes 7 can be conical or can comprise a conical interior thread. The bone plate 1 additionally comprises under-dimensioned threaded screw holes 15 apt to receive fasteners so as to provide means for attachment of a bone healing sensor. In other alternative embodiments the plate holes 7 may have different sizes to receive bone screws of different diameters.

Exemplarily, but not limiting, the slot 8 has a width W of about 0.3 mm measured at the lower surface 2 of the bone plate 1 in the direction of the longitudinal axis 6. The width W of the slot 8 is chosen so as to allow the bone plate 1 to bend longitudinally—additionally to the intrinsic bendability of a similar unslotted plate—at most to about 10° and to permit a shortening of the length of the lower surface 2 of at most about 1 mm upon complete closure of the slot 8 at the lower surface 2 of the bone plate 1 so that the width W measured at the lower surface 2 is equal to 0. Thereby, a force of about 200 N, acting essentially parallel to the longitudinal axis 6 of the bone plate 1 with an offset of about 20 mm from the lower surface 2 of the bone plate 1 is sufficient to close the slot 8 at the lower surface 2 of the bone plate 1 so that the width W is equal to 0. The slot dimensions in the area of the undercut feature 9 are such that lengthening of the lower surface 2 is exemplarily, but not limiting, limited to at most 2 mm when the bone plate 1 is bent longitudinally in a direction aimed at widening the slot 8.

Figure 9:
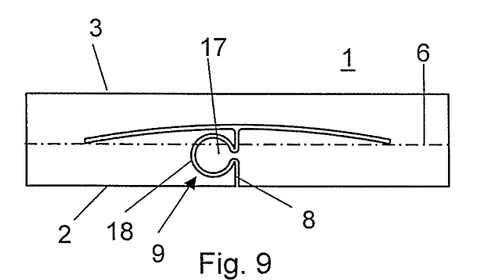
FIG. 9 illustrates a lateral view of a central portion of a further embodiment of the bone plate according to the invention.
Figure 10:
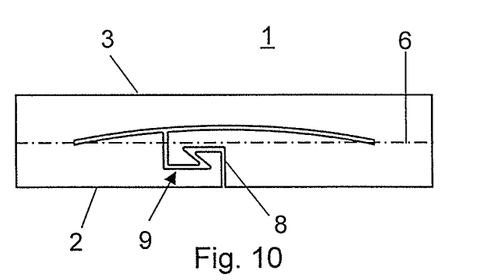
FIG. 10 illustrates a lateral view of a central portion of a further embodiment of the bone plate according to the invention.
Figure 11:
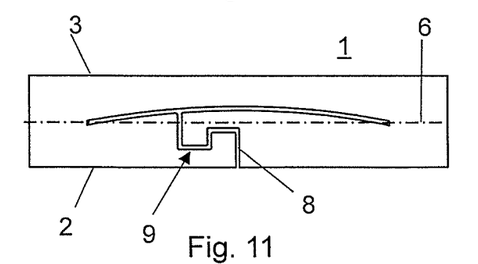
FIG. 11 illustrates a lateral view of a central portion of a further embodiment of the bone plate according to the invention.
Figure 12:
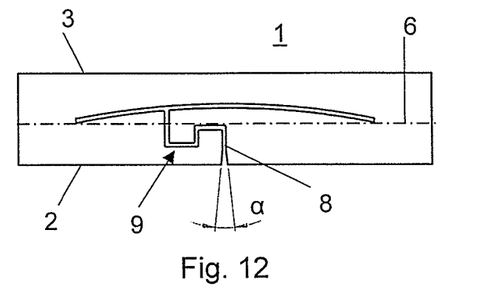
FIG. 12 illustrates a lateral view of a central portion of a further embodiment of the bone plate according to the invention.

FIGS. 9-12 illustrate alternative embodiments of the bone plate 1 according to the invention, which differ from the embodiment of FIGS. 1-6 only in a different configuration of the slot 8 viewed in a plane parallel to the central plane 16 between the lateral surfaces 4,5. Thereby, FIG. 10 illustrates an undercut feature 9 with a Z-shape in a plane parallel to the longitudinal axis 6 and to the central plane 16 between the lateral surfaces 4,5 instead of an S-shape and FIG. 9 illustrates an undercut feature 9 with an Ω-shape in a plane parallel to the longitudinal axis 6 and to the central plane 16 between the lateral surfaces 4,5. This Ω-shaped undercut feature 9 forms a nose 17 which protrudes from one of the rigid sections 11*a* (FIG. 3) of the bone plate 1 along the longitudinal axis 6 and which has an enlarged free end. The adjoining end of the other rigid section 11*b* (FIG. 3) of the bone plate 1 is concavely formed so as to form an encompassment 18 that receives the nose 17 in such a way that movement of the nose 17 relative to the encompassment 18 is limited in both directions along the longitudinal axis 6 of the bone plate 1. In the undeformed state of the bone plate 1 the slot 8 extends between the nose 17 and the encompassment 18 with the width W measured at the lower surface 2. The encompassment 18 encloses the nose 17 more than 180° in a view orthogonal to the central plane 16 between the lateral surfaces 4,5 so that bending of the bridging portion 12 is limited in both directions, i.e. in a first direction where the maximum tensile forces occur on the upper surface 3 and in a second direction where the maximum compressive forces occur on the upper surface 3 so as to provide resistance against tensile forces and valgus bending. Due to the S-shape, Z-shape or Ω-shape of the undercut feature two adjoining projections are formed which additionally provide resistance against torsion of the bone plate. FIG. 11 illustrates a slot 8 which is similarly configured as the slot 8 of FIGS. 1-6 with the shape of a "T" in an upper portion of the bone plate 1, i.e. in a portion of the bone plate 1 closer to the upper surface 3 of the bone plate 1 but the free end of the vertical leg of the "T" runs into the S-shaped portion of the slot 8 in such a way that the vertical section of the slot 8 into which one bow of the "S" runs and which extends from the lower surface 2 of the bone plate 1 towards the upper surface 3 is located centrally between the two horizontal legs of the "T". A further alternative embodiment is illustrated in FIG. 12 which differs from the embodiment of FIG. 11 only therein that the walls of the slot 8 at the lower surface 2 of the bone plate 1 are angulated with respect to each other by an angle a such that they become parallel upon closing of the slot 8. By this means the contact area between the walls of the slot 8 is increased upon closure of the slot 8 when a load is applied to the bone plate 1 so that metal wear at the contact area is reduced.

Figure 8:
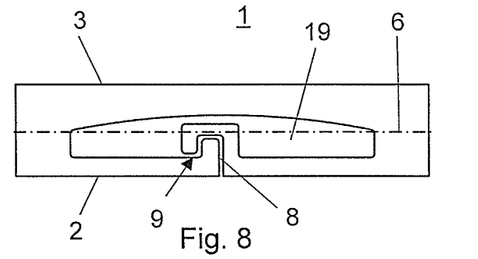
FIG. 8 illustrates a lateral view of a central portion of again another embodiment of the bone plate according to the invention.

As mentioned above, the width of the slot 8 may significantly widen towards the upper surface 3 of the bone plate 1 e.g. in a T-shape to form a stress distribution feature. In an alternative embodiment of the bone plate 1 illustrated in FIG. 8 the width W of the slot 8 measured in a plane parallel to the longitudinal axis 6 and to the central plane 16 between the lateral surfaces 4,5 is significantly enlarged along the horizontal legs of the T-shaped slot 8. By this means the flexible section 10 of the bone plate 1 comprises a compartment 19 extending from the top side 14 of the slot 8. The compartment 19 is open via the slot 8 at the lower surface 2 of the bone plate 1. The compartment 19 is suitable to accommodate one or more sensors (not shown), preferably for measuring strain, displacement, load or pressure or temperature. Alternatively or additionally the compartment 19 is suitable to accommodate one or more actuators, to alter the implant's mechanical properties, or store drugs for controlled release or to provide space for callus growth.

In further alternative embodiments the slot 8 is fully or partially covered by an elastic biocompatible membrane, wherein the membrane is impermeable for micro and nano metallic wear particles so that potential wear particles generated through intermittent slot closing contact can be confined in the membrane. Alternatively, the slot 8 may be filled with a softer material to reduce the "dead space" and to bind wear particles.

According to the method of manufacturing the bone plate 1 according to the invention the slot 8 is formed using a wire-erosion or waterjet cutting process to generated the slot 8 by penetrating the bone plate 1 with an eroding or waterjet cutting instrument into one of the lateral surfaces 4; 5 and guiding it in a directed straight manner to the opposite lateral surface thereby creating a through going slot 8.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A bone plate with a lower surface, an upper surface, a maximum thickness T measured between the lower and upper surfaces, a left lateral surface, a right lateral surface, a longitudinal axis and a plurality of plate holes running from the lower surface to the upper surface, wherein the bone plate further comprises a slot with an opening in the lower surface, wherein the slot extends through the bone plate from the left lateral surface to the right lateral surface and has a width W measured in a plane parallel to the longitudinal axis and a central plane between the left lateral surface and the right lateral surface, and wherein:
   (i) the slot includes an inner surface that defines a hollow space extending through the bone plate from the left lateral surface to the right lateral surface through which a straight line is passable without contacting the inner surface of the slot; and
   (ii) the slot comprises an undercut feature limiting the opening of the slot when the bone plate is bent longitudinally in a direction aimed at widening the slot.

2. The bone plate according to claim 1, wherein the width W of the slot measured in the plane parallel to the longitudinal axis and to the central plane between the left lateral surface and the right lateral surface is variable.

3. The bone plate according to claim 1, wherein the undercut feature has an S-shape in the plane parallel to the longitudinal axis and to the central plane between the left lateral surface and right lateral surface.

4. The bone plate according to claim 1, wherein the undercut feature has a Z-shape in the plane parallel to the longitudinal axis and to the central plane between the left lateral surface and right lateral surface.

5. The bone plate according to claim 1, wherein the undercut feature has an Ω-shape in the plane parallel to the longitudinal axis and to the central plane between the left lateral surface and right lateral surface.

6. The bone plate according to claim 1, wherein the dimensions of the undercut feature are such that lengthening of the lower surface is limited to at most 3 mm when the bone plate is bent longitudinally in a direction aimed at widening the slot.

7. The bone plate according to claim 1, wherein the dimensions of the undercut feature are such that lengthening of the lower surface is limited to at most 1 mm when the bone plate is bent longitudinally in a direction aimed at widening the slot.

8. The bone plate according to claim 1, wherein the width W of the slot is in a range of 0.1 to 1.3 mm measured at the lower surface of the bone plate in a direction of the longitudinal axis.

9. The bone plate according to claim 1, wherein the width W of the slot is in a range of 0.15 to 0.30 mm measured at the lower surface of the bone plate in a direction of the longitudinal axis.

10. The bone plate according to claim 1, wherein the slot is configured with the shape of a "T" in an upper portion of the bone plate, wherein a free end of the vertical leg of the "T" runs into the undercut feature of the slot and the two horizontal legs of the "T" extend in a direction of the longitudinal axis of the bone plate.

11. The bone plate according to claim 10, wherein the two horizontal legs of the "T" are curved.

12. The bone plate according to claim 1, wherein the slot is configured with the shape of an "L" in an upper portion of the bone plate, wherein a free end of the vertical leg of the "L" runs into the undercut feature of the slot and the horizontal leg of the "L" extends in a direction of the longitudinal axis of the bone plate.

13. The bone plate according to claim 12, wherein the horizontal leg of the "L" is curved.

14. The bone plate according to claim 1, wherein walls of the slot at the lower surface of the bone plate are angulated with respect to each other such that they become parallel upon closing of the slot.

15. The bone plate according to claim 1, wherein the dimensions of the slot are such that a length of the lower surface is shortened at most 1 mm upon complete closure of the slot at the lower surface of the bone plate so that the width W measured at the lower surface is equal to 0.

16. The bone plate according to claim 1, wherein the dimensions of the slot are such that a length of the lower surface is shortened at most 0.3 mm upon complete closure of the slot at the lower surface of the bone plate so that the width W measured at the lower surface is equal to 0.

17. The bone plate according to claim 1, wherein the slot allows the plate to bend longitudinally at least to the amount of 1.0°.

18. The bone plate according to claim 1, wherein the slot allows the plate to bend longitudinally at least to the amount of 1.5°.

19. A method of manufacturing the bone plate according to claim 11, comprising a step of forming the slot using a wire-erosion process.

20. A method of manufacturing the bone plate according to claim 1, comprising a step of forming the slot using a waterjet cutting process.

* * * * *

UNITED STATES PATENT AND TRADEMARK OFFICE
CERTIFICATE OF CORRECTION

PATENT NO. : 12,324,613 B2
APPLICATION NO. : 17/780576
DATED : June 10, 2025
INVENTOR(S) : Markus Windolf et al.

Page 1 of 1

It is certified that error appears in the above-identified patent and that said Letters Patent is hereby corrected as shown below:

In the Claims

In Column 11, Line 28, delete "to claim 11" and add --to claim 1--

Signed and Sealed this
Twenty-sixth Day of August, 2025

Coke Morgan Stewart
*Acting Director of the United States Patent and Trademark Office*